(12) United States Patent
Haibach, Jr. et al.

(10) Patent No.: US 11,896,764 B2
(45) Date of Patent: Feb. 13, 2024

(54) RESPIRATORY MASK HAVING A MAGNETICALLY SUPPORTED CUSHION

(71) Applicant: KONINKLIJKE PHILIPS N.V., Eindhoven (NL)

(72) Inventors: Richard Thomas Haibach, Jr., Verona, PA (US); Sander Theodoor Pastoor, Utrecht (NL); Christoph Dobrusskin, Eindhoven (NL); Andrew Blake Kittridge, Mcmurray, PA (US); Jerome Matula, Jr., Apollo, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 584 days.

(21) Appl. No.: 16/815,047

(22) Filed: Mar. 11, 2020

(65) Prior Publication Data
US 2020/0215287 A1 Jul. 9, 2020

Related U.S. Application Data

(63) Continuation of application No. 14/429,148, filed as application No. PCT/IB2013/058712 on Sep. 20, 2013, now Pat. No. 10,617,837.

(60) Provisional application No. 61/703,974, filed on Sep. 21, 2012.

(51) Int. Cl.
*A61M 16/06* (2006.01)
*A61M 16/08* (2006.01)

(52) U.S. Cl.
CPC .... *A61M 16/0622* (2014.02); *A61M 16/0683* (2013.01); *A61M 16/0816* (2013.01); *A61M 16/0633* (2014.02); *A61M 2205/0272* (2013.01)

(58) Field of Classification Search
CPC ....... A62B 18/02; A62B 18/025; A62B 23/02; A62B 23/025
See application file for complete search history.

(56) References Cited

U.S. PATENT DOCUMENTS

| 3,181,895 | A | 5/1965 | Cator |
| 3,938,614 | A | 2/1976 | Ahs |
| 4,260,180 | A | 4/1981 | Halushka et al. |
| 7,546,837 | B2 | 6/2009 | Busch et al. |
| 7,793,987 | B1 * | 9/2010 | Busch ................. A61M 16/161 |
| | | | 285/9.1 |
| 8,863,745 | B2 | 10/2014 | Dantanarayana et al. |
| 9,724,488 | B2 | 8/2017 | Guney |
| 9,987,450 | B2 | 6/2018 | Carroll et al. |
| 2003/0196655 | A1 | 10/2003 | Ging et al. |
| 2003/0196656 | A1 | 10/2003 | Ging et al. |
| 2004/0089302 | A1 | 5/2004 | Foss |
| 2004/0112377 | A1 | 6/2004 | Amarasinghe et al. |

(Continued)

FOREIGN PATENT DOCUMENTS

| WO | 2005123166 A1 | 12/2005 |
| WO | 2010099790 A1 | 9/2010 |

(Continued)

*Primary Examiner* — Valerie L Woodward
(74) *Attorney, Agent, or Firm* — Michael W. Haas

(57) ABSTRACT

A patient interface face contact element includes a surface for contacting the face of a patient and a connection face for coupling the patient interface face contact element to a support using a magnetic coupling. The support is also provided as well as the complete patient interface. Headgear strap clips can also be retained magnetically.

11 Claims, 4 Drawing Sheets

(56) References Cited

U.S. PATENT DOCUMENTS

| | | | |
|---|---|---|---|
| 2006/0118117 A1* | 6/2006 | Berthon-Jones | A61M 16/0057 128/206.27 |
| 2006/0174892 A1 | 8/2006 | Chiesa et al. | |
| 2006/0283455 A1 | 12/2006 | Henderson et al. | |
| 2006/0283456 A1* | 12/2006 | Geiselhart | A61M 16/06 128/205.27 |
| 2007/0062537 A1 | 3/2007 | Chiesa et al. | |
| 2008/0060649 A1* | 3/2008 | Veliss | A61M 39/08 128/207.18 |
| 2008/0264413 A1* | 10/2008 | Doherty | A61M 16/0051 128/202.27 |
| 2009/0145429 A1 | 6/2009 | Ging et al. | |
| 2010/0000534 A1 | 1/2010 | Barlow et al. | |
| 2010/0018534 A1 | 1/2010 | Brackenreg et al. | |
| 2010/0307497 A1 | 12/2010 | Busch et al. | |
| 2010/0307505 A1 | 12/2010 | Materna et al. | |
| 2011/0067704 A1 | 3/2011 | Benjafield et al. | |
| 2011/0174310 A1 | 7/2011 | Biener et al. | |
| 2012/0080035 A1 | 4/2012 | Edwards et al. | |
| 2012/0090617 A1* | 4/2012 | Matula, Jr. | A61M 16/0611 128/206.21 |
| 2012/0167892 A1 | 7/2012 | Matula | |
| 2012/0222680 A1* | 9/2012 | Eves | A61M 16/0644 128/206.24 |
| 2013/0263858 A1* | 10/2013 | Ho | A61M 16/0683 128/205.25 |
| 2014/0069434 A1 | 3/2014 | Neff | |

FOREIGN PATENT DOCUMENTS

| | | |
|---|---|---|
| WO | 2011022779 A1 | 3/2011 |
| WO | 2011030250 A1 | 3/2011 |
| WO | 2013179267 A1 | 12/2013 |

* cited by examiner

RESPIRATORY MASK HAVING A MAGNETICALLY SUPPORTED CUSHION

CROSS-REFERENCE TO RELATED APPLICATIONS

This application is a continuation under 35 U.S.C. § 120 of U.S. patent application Ser. No. 14/429,148, filed Mar. 18, 2015, which claims priority to PCT Application PCT/IB2013/058712 filed Sep. 20, 2013, which claimed priority to the provisional U.S. Patent Application No. 61/703,974, filed Sep. 21, 2012, the contents of which are incorporated herein by reference.

FIELD OF THE INVENTION

The present invention relates to patient interfaces for transporting a gas to and/or from an airway of a user.

BACKGROUND OF THE INVENTION

There are numerous situations where it is necessary or desirable to deliver a flow of breathing gas non-invasively to the airway of a patient, i.e. without inserting a tube into the airway of the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA).

Non-invasive ventilation and pressure support therapies involve the placement of a patient interface device including a mask component on the face of a patient. The mask component may be, without limitation, a nasal mask that covers the patient's nose, a nasal pillow/cushion having nasal prongs that are received within the patient's nostrils, a nasal/oral mask that covers the nose and mouth, or a full face mask that covers the patient's face. The patient interface device interfaces between the ventilator or pressure support device and the airway of the patient, so that a flow of breathing gas can be delivered from the pressure/flow generating device to the airway of the patient.

Such devices are typically maintained on the face of a patient by headgear having one or more straps adapted to fit over/around the patient's head.

FIG. 1 shows a typical system to provide respiratory therapy to a patient. This is termed a "patient interface assembly".

The assembly 2 includes a pressure generating device 4, a delivery conduit 16 coupled to an elbow connector 18, and a patient interface 10. The pressure generating device 4 is structured to generate a flow of breathing gas and may include, without limitation, ventilators, constant pressure support devices (such as a continuous positive airway pressure device, or CPAP device), variable pressure devices, and auto-titration pressure support devices.

Delivery conduit 16 communicates the flow of breathing gas from pressure generating device 4 to patient interface 10 through the elbow connector 18. The delivery conduit 16, elbow connector 18 and patient interface 10 are often collectively referred to as a patient circuit.

The patient interface 10 includes a mask 12, which in the exemplary embodiment is a nasal and oral mask covering the nose and mouth. However, any type of mask, such as a nasal-only mask, a nasal pillow/cushion or a full face mask, which facilitates the delivery of the flow of breathing gas to the airway of a patient, may be used as mask 12. The mask 12 includes a cushion 14 coupled to a shell 15. The cushion 14 is made of a soft, flexible material, such as, without limitation, silicone, an appropriately soft thermoplastic elastomer, a closed cell foam, or any combination of such materials. An opening in shell 15, to which elbow connector 18 is coupled, allows the flow of breathing gas from pressure generating device 4 to be communicated to an interior space defined by the shell 15 and cushion 14, and then to the airway of a patient.

The assembly 2 also includes a headgear component 19, which in the illustrated embodiment is a two-point headgear. Headgear component 19 includes a first and a second strap 20, each of which is structured to be positioned on the side of the face of the patient above the patient's ear.

Headgear component 18 further includes a first and a second mask attachment element 22 to couple the end of one of the straps 20 to the respective side of the mask 12.

It is well known to include a forehead support to spread the required forces over a larger area. In this way, an additional cushion support on the forehead balances the forces put by the mask around the nose or nose and mouth. This can be used to address a problem that the headgear force vectors necessary to achieve a robust and stable seal against the face of the patient can cut a straight line near the corners of a patient's eyes, which can be uncomfortable and distracting.

The seal that encloses the face or part of the face needs to be replaceable, as frequent use induces wear and tear. A problem is that on one hand the fit of the replacement part with the mask shell 15 has to be relatively loose, so as to enable an easy exchange. On the other hand, however, the replacement part should fit to the mask shell tightly as the two parts have to provide an airtight seal with each other.

Typically, silicon parts are used which have to be propped into place with much dexterity. This can be difficult for a user to achieve.

SUMMARY OF THE INVENTION

According to the invention, there is provided a patient interface face contact element and a patient interface support as claimed in the independent claims.

In one aspect, the invention provides a patient interface face contact element comprising a surface for contacting the face of a patient, and a connection face for coupling the patient interface face contact element to a support, wherein the contact element comprises a magnetic coupling arrangement associated with the connection face.

In another aspect, the invention provides a patient interface support comprising a coupling surface for coupling to a patient interface face contact element, wherein the support comprises a magnetic coupling arrangement associated with the coupling surface.

The invention provides a fixation method for a patient interface face contact element, which is the replaceable part of the patient interface. The interface face contact element can be a mask seal or a mask support cushion, and these are frequently replaced due to wear and tear. The invention provides an arrangement which allows the replaceable parts to be easily removable as well as providing a secure and airtight fit.

The magnetic coupling arrangement can comprise magnets which are inserted into retaining pockets or moulded into the structure. The magnetic coupling arrangement of the face contact element can instead comprise a magnet arrangement to be applied against a back of the connection face.

In one arrangement, the support comprises magnetic elements and the face contact element comprises ferromagnetic regions for interfacing with the magnetic elements. In another arrangement, the face contact element comprises magnetic elements and the support comprises ferromagnetic regions for interfacing with the magnetic elements. In another arrangement, the face contact element and the support each comprise magnetic elements with opposite poles facing each other.

The invention also provides a patient interface for communicating a gas to the nose or the nose and mouth of a patient, comprising a support and a face contact element, wherein the face contact element and/or the support are in accordance with the invention.

The most basic version of the patient interface simply has the support and face contact element magnetically coupled together. However, an alternative embodiment has at least one headgear strap clip, wherein the clip is adapted to be retained magnetically by the magnetic coupling arrangement of the support and/or the face contact element.

In this way, a magnetic coupling of three components is provided; the clip, the support and the face contact element. The use of a releasable headgear strap enables the patient interface to be fitted more easily.

The face contact element, the support and the clip can be stacked, and the magnetic coupling arrangement then comprises at least one stack of a magnet element or elements and a ferromagnetic element or elements, with the face contact element, the support and the clip each having a respective one of the elements. In this way, the magnetic coupling arrangement comprises one or more attachment points, at which the three components are magnetically coupled together. For this purpose, the middle component (which is the support) can have a magnet and the other components can have ferromagnetic elements. However, any other configuration is possible, with one, two or three magnets, and with none, one or two ferromagnetic elements.

The patient interface then can include a headgear strap arrangement for coupling to the headgear strap clip or clips.

The face contact element, the support and the clip can each comprise non-planar physical alignment features. These can be used to resist decoupling of the magnetic fixing resulting from the forces expected in normal use.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a patient interface face contact element comprising a surface for contacting the face of a patient, and a connection face for coupling the patient interface face contact element to a support using a magnetic coupling. The invention also provides a patient interface support comprising a coupling surface for coupling to a patient interface face contact element using a magnetic coupling. Headgear strap clips can also be retained magnetically.

Figure 1:
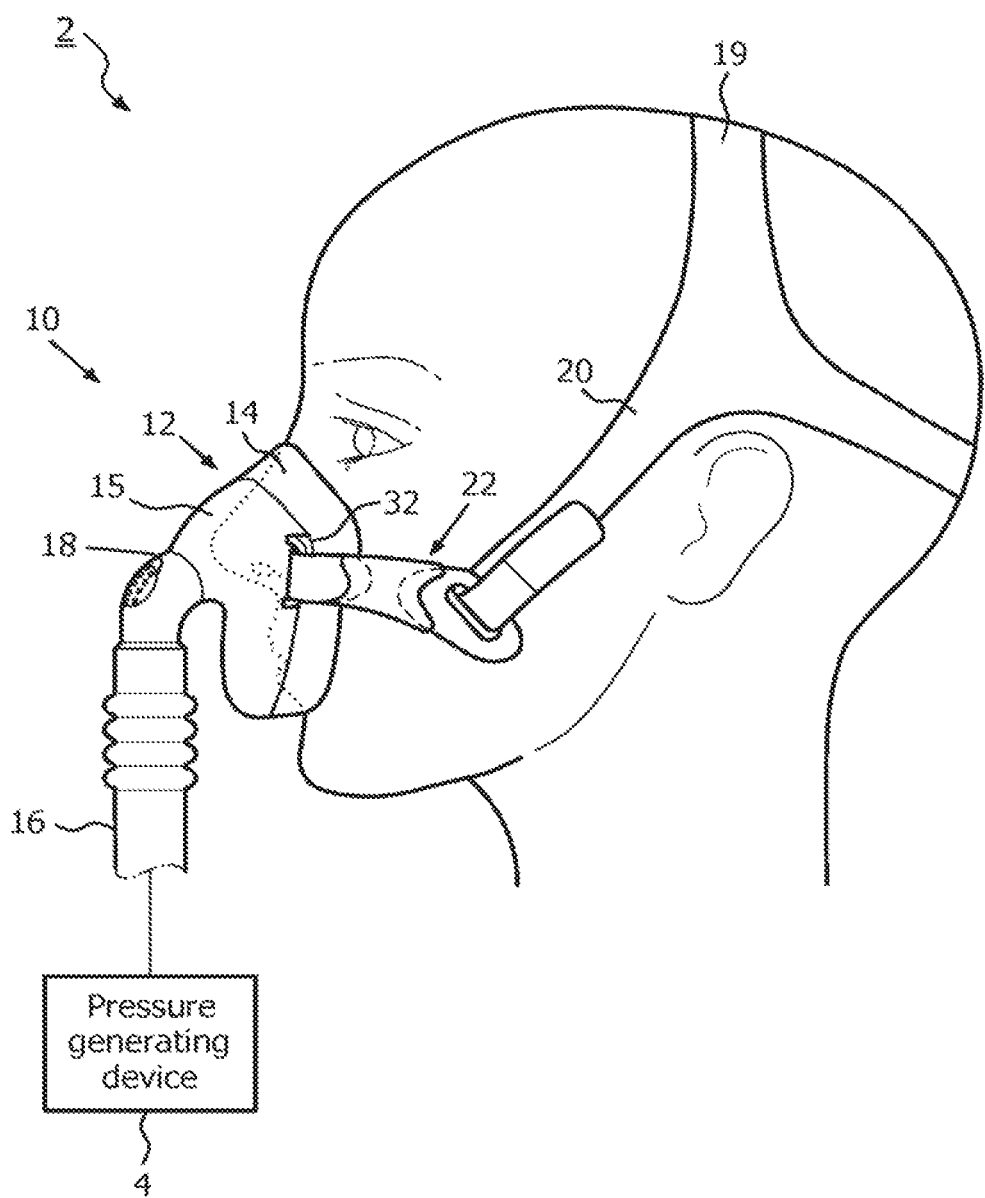
FIG. 1 shows a known patient interface.
Figure 2:
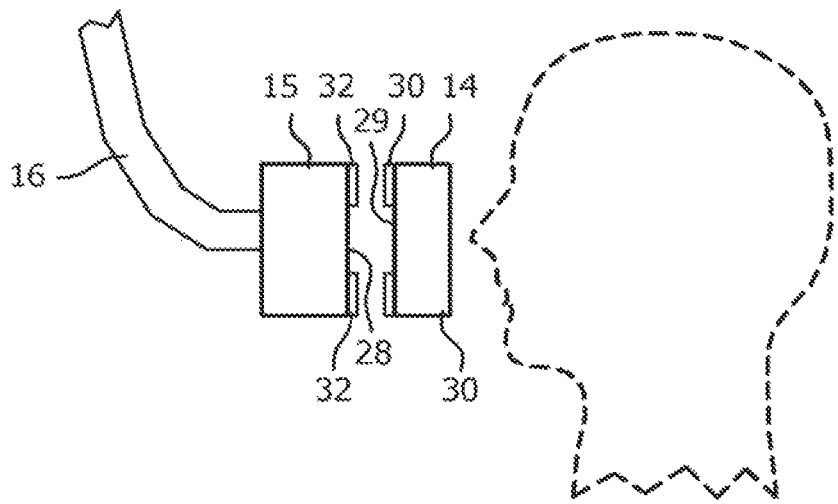
FIG. 2 shows a first example of patient interface of the invention.

A first embodiment is shown schematically in FIG. 2, in which the same reference numbers are used as in FIG. 1.

The patient interface comprises the mask shell 15 and the cushion 14. The mask shell 15 defines a plane substantially parallel to the face of the user. This is a coupling surface 28 the shell. One side of the shell 15 away from the user's face is fitted with a supply of air from delivery tube 16, and the other side facing the user's face is coupled by the coupling surface 28 to the cushion 14 that fits over the nose and/or mouth of the user.

The cushion 14 includes a contact surface that is designed to seal against the user's face, and an opposing connection face 29 where it couples to the coupling surface 28 of the mask shell 15.

The mask shell 15 is connected to the cushion 14 with a set of magnetic fittings, comprising first magnetic elements 30 of the cushion 14 and second magnetic elements 32 of the shell 15. This allows the seal and cushion 14 to be easily removed and replaced even by an untrained user.

Various designs for the magnetic coupling are possible. For example, the magnetic coupling can also provide a self-alignment function to make the connection more straightforward.

FIG. 3 shows different ways to integrate the magnets into the structure of the shell and cushion.

Figure 3A:
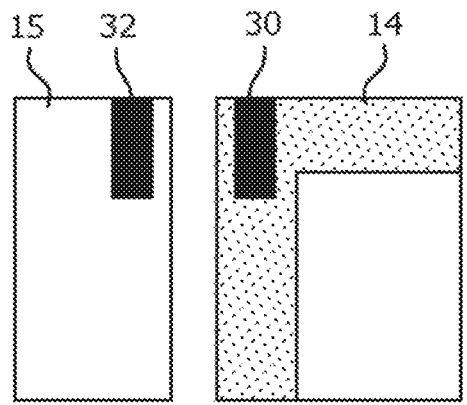
FIG. 3 shows different ways to configure the magnetic coupling in the patient interface of FIG. 2.

In FIG. 3A, the cushion 14 is a silicon seal part whereas the shell 15 is a rigid plastics part. The magnets 30 for the cushion 14 are pushed into respective pockets of the silicon cushion, and the magnets 32 for the shell are pushed into the respective pockets of the shell.

Figure 3B:
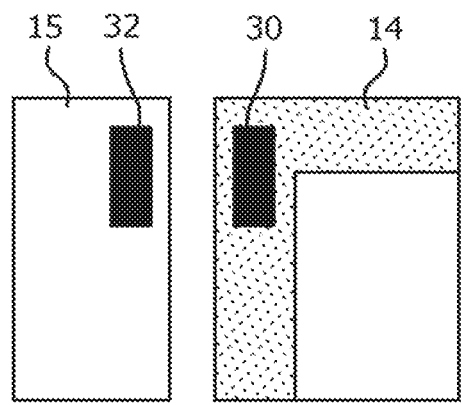

In FIG. 3B, the magnets 30,32 are moulded into the silicon cushion and into the mask shell.

Figure 3C:
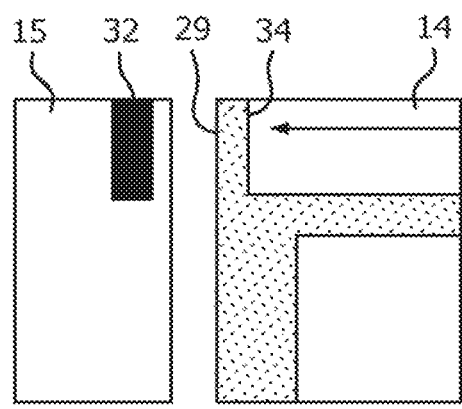

In FIG. 3C, the magnets 30 for the cushion 14 are provided as a separate arrangement which is placed over the cushion after bringing the shell 15 and cushion 14 together. The magnetic arrangement 30 can comprise a set of discrete magnets or a single ring which incorporates separate magnets. This can then be applied against a back 34 of the connection face 29 to clamp the connection face 29 against the coupling surface 28 of the mask shell 15.

Thus, in these examples the magnets 32 of the shell and the magnets 30 of the cushion 14 can injection moulded or inserted into pockets. The magnets can instead be fixed to the mask shell and cushion using movable or flexible coupling elements.

In the examples of FIG. 3A to 3C, the replaceable part is the flexible cushion part, which is typically silicone. However, the replaceable part can include a rigid connection part to which the cushion is permanently attached.

The coupling between the replaceable part and the shell 15 can then include indexing features so that the coupling can only be made with the correct relative positioning, at which the magnetic coupling is most effective.

Figure 3D:
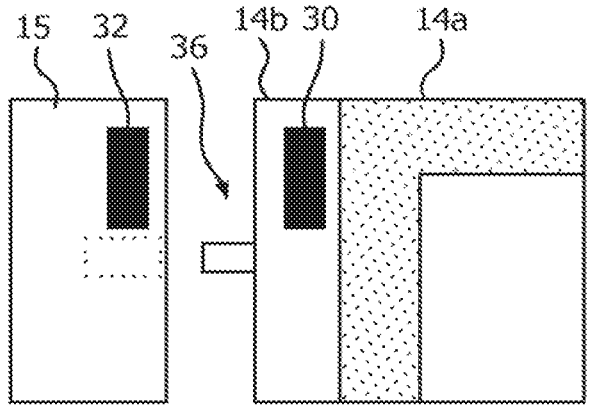

FIG. 3D shows an example in which the cushion 14 has a flexible part 14*a* and a rigid part 14*b*, and the magnets 30 are provided in the rigid part 14*b*. Indexing features can ensure the correct relative positioning in a simple manner, for example with corresponding projections and recesses, as schematically shown as 36.

The magnets themselves can also perform an indexing function, by providing suitable orientation and/or shaping of the magnets.

The magnetic coupling can comprise magnets on one side and ferromagnetic material on the other side, or else magnets on both sides, with opposite poles. Thus, only one of the two elements (shell and cushion) needs to have magnets. Since the shell and cushion are otherwise non-metal (e.g. plastics and silicone), ferromagnetic materials can be used for magnetic attraction to function in the same way as having opposing magnets.

Additional seal fittings may be used to improve the quality of the airtight seal between the cushion and the mask shell. For example a compressible seal can be provided on one or both of the shell and cushion so that the magnetic attraction force is used both to retain the parts together but also to actively compress a seal between the parts. An additional sealing component can be provided for placing around the magnetic coupling. However, any additional components should be easy for user the since otherwise the object of providing the magnetic coupling is defeated.

This embodiment of the invention can be embodied as a replacement cushion alone, which is supplied separately to the rest of the patient interface assembly, or it can be embodied as a mask shell part, or as complete a patient interface (i.e. a mask with shell and cushion), or as a full system.

This embodiment of the invention relates to the interface between the mask shell and the cushion. For this reason, other components have not been shown in FIG. 2, such as the headgear, gas supply, or a forehead support if desired. It will be appreciated that all of these known components and all of their known variations can be applied to the arrangement of the invention.

The invention can be applied to a nasal mask, an oral mask, a nasal/oral mask or a full face mask. The magnetic coupling can be applied to any part that contacts the user's face and is therefore prone to wear and tear and therefore should be replaceable. In the examples above, permanent magnets are used to form the magnetic coupling. Electromagnets could also be used. By reversing the electromagnet drive current in one component, an inverse magnetic coupling can be created to assist the decoupling operation. Thus, electromagnets can be used to provide the coupling force but also to assist decoupling.

In the examples shown, the magnets face each other, so that the plane of the magnetic contact faces are perpendicular to the intended direction of application and removal of the magnetic coupling. Instead, the magnets can be arranged so that the coupling and/or decoupling is accompanied by a sliding of the two magnets relative to each other. This can provide an arrangement which is easier to separate. In this case, the magnetic faces are no longer perpendicular to the coupling direction, but they are at an angle to the coupling direction. The magnetic coupling can be pivotable between an orientation in which the magnetic faces are perpendicular to the coupling direction (for the coupled configuration) and one in which they are angled to the coupling direction, to facilitate removal. Thus, for component removal, the magnetic coupling can be rotated so that the decoupling can be based on sliding the magnets apart rather than pulling them apart.

The material of the seal can be used to create a hinge structure for this purpose. This hinge is then manually moved during component removal.

As outlined above, this embodiment of the invention enables replacement of component parts, in particular the seal part against the user's face. It may be preferred that the part to be replaced does not contain the magnet, so that the magnet can be re-used. This is for example the case with the design of FIG. 3C, but other designs which provide the magnet of the replaceable part as a non-integrated component are also possible.

The embodiment described above provides magnetic coupling of the mask cushion 30 to the shell 15.

In some known designs, the mask attachment element 22 (see FIG. 1) is detachable from the shell 15 to enable easier fitting of the patient interface 10. Removable headgear clips are known for this purpose. For example, these headgear clips can be snapped on using a talon clip and post. For example, there may be two attachment elements 22 on each side of the shell 15 (instead of the one shown in FIG. 1) with one on each side being detachable to avoid having to pull straps all the way over the head. A strap over the top of the head can be fixed to the shell, whereas a strap to go around the back of the head can be detachable.

The magnetic design described above can be extended so that a individual magnetic coupling points provide an attachment location for both the mask cushion (as described above) and also for a detachable headgear strap. In this way, a multifunction embedded magnet system is provided, which can improve the assembly of both headgear mask clips, and the cushion.

In the same way as for the example above, the self-guiding feature of a pair of magnets or else a magnet and a ferrous metal mating feature eases the assembly process for the user.

Figure 4A:
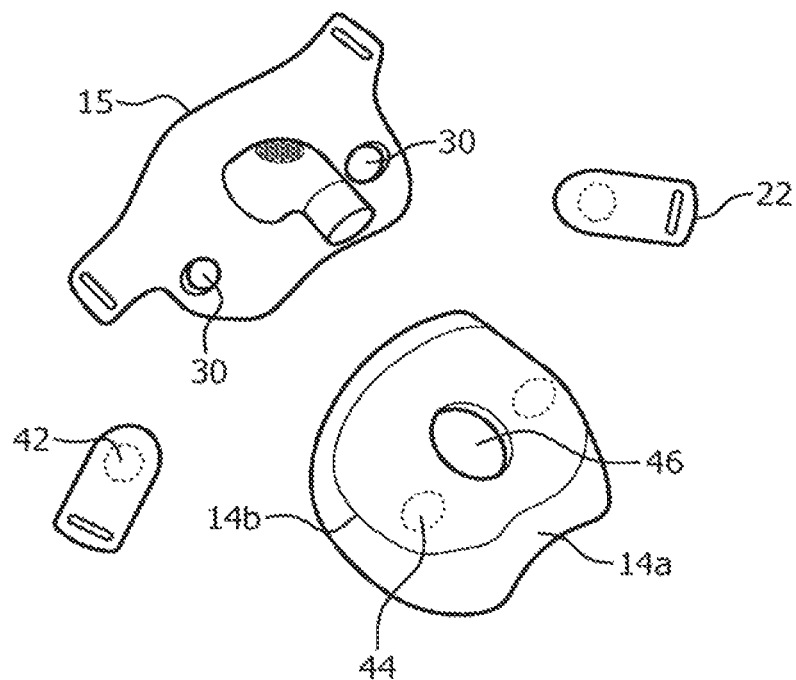
FIG. 4 shows a second example of patient interface of the invention, in exploded view as well as in assembled view.
Figure 4B:
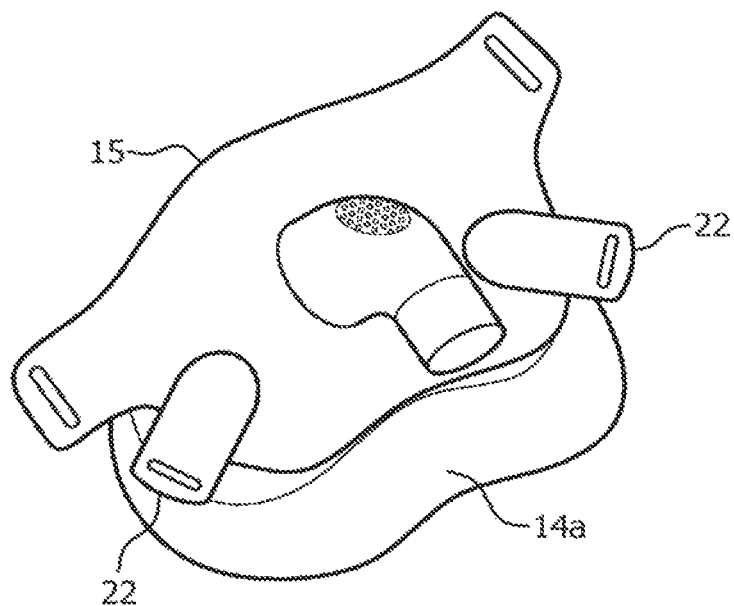

FIG. 4 shows a second example of patient interface of the invention provide magnetic clips, with an exploded view in FIG. 4A and an assembled view in FIG. 4B. The same components are given the same reference numbers as in FIGS. 1 to 3.

As shown in the example of FIG. 4A, the mask shell 15 is provided with the magnets 30. They are used as attachments to both sides of the mask shell 15. To the inside of the mask shell, the cushion 14a is removably attached, and to the outside of the mask shell the mask attachment elements 22 (in the form of clips) are attached. The headgear straps (shown in FIG. 1 but not shown in FIG. 4A or FIG. 4B) attach to these clips 22.

In the example of FIG. 4A and FIG. 4B, the cushion 14a is attached to a rigid part 14b (as already shown in FIG. 3D) in the form of a hub, and the hub 14b and cushion 14a are together a disposable part of the patient interface assembly.

The clips 22 are each provided with a magnet (or multiple magnets), or a ferrous metal portion 42 which attaches over a corresponding magnet 30 of the shell 15. Similarly, the hub 14b has magnets, or ferrous metal portions 44 which attach beneath the magnets 30 of the shell 15.

Thus, a set of magnets, such as rare earth magnets, is embedded into the shell 15 near each headgear clip 22. The headgear clips have a mating feature with the shell, centered on the magnet, and the hub 14b also has a mating feature centred on the magnet. This allows the hub 14b to be self-guided on the shell, and the clips 22 to be self guided on the shell independently.

The three coupled parts need at least one magnet, and the other parts need to be ferrous. However two or three magnets can be used at each coupling. Any combination of magnet and ferrous contact will suffice, but preferably with each contact including at least one magnet. The most efficient implementation has a single magnet in the middle of the three layer stack as shown, but there can be two or three magnets in the three layer stack.

Thus, a preferred implementation has a magnet embedded into the shell 15 and steel discs in the hub 14b and the clips 22. If multiple magnets are instead used, the polarity of the magnets must of course be aligned during manufacturing.

Each of the components can use an overmolding process to place the magnet or steel inside the respective component, or else a press fit secondary process can be used. The preferred type of magnet is an NdFeB magnet, due to the low cost and high pull strength.

Figure 5A:
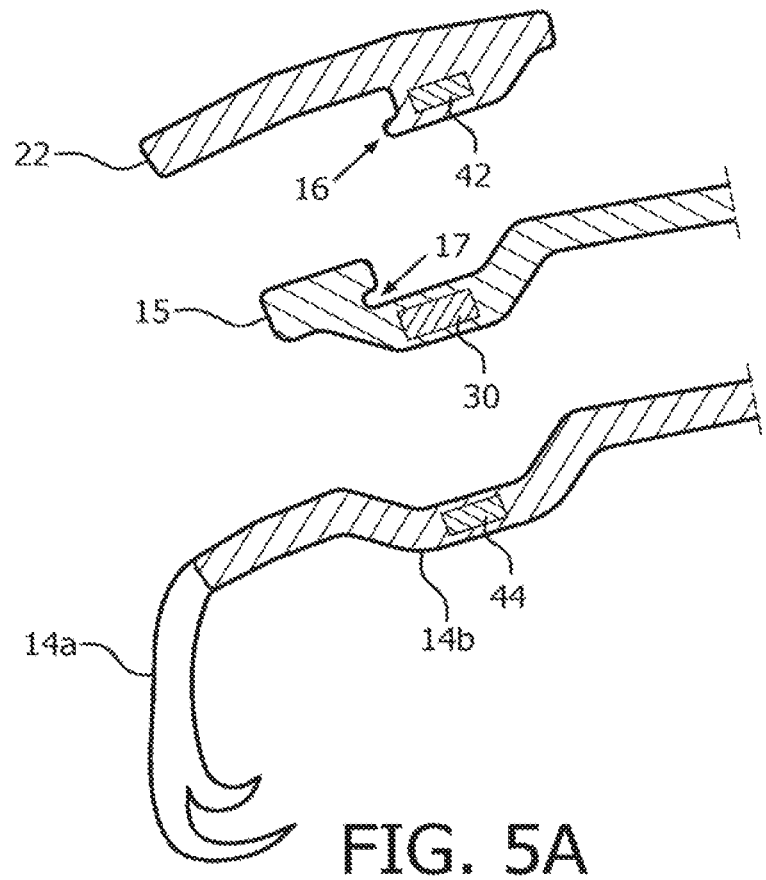
FIG. 5 shows the magnetic coupling arrangement used in the patient interface of FIG. 4 in more detail, in detached and attached configurations.
Figure 5B:
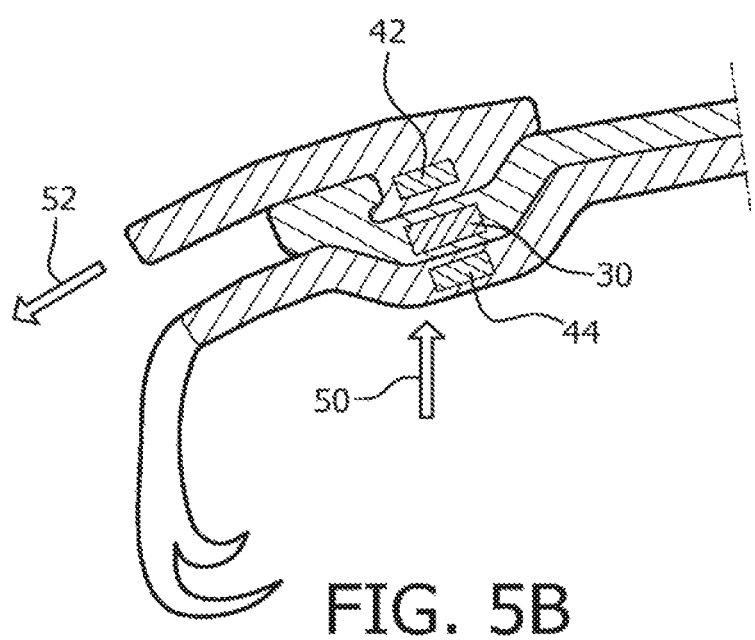

FIG. 5 shows the preferred magnetic coupling arrangement used in the patient interface of FIG. 4 in more detail, in detached configuration in FIG. 5A and in attached configuration in FIG. 5B.

FIG. 5A shows that the shell 15 has an interlocking (non-planar) shape, rather than a flat planar profile. It has a projection one side and a recess on the other. The projection faces the cushion in the example shown, and the hub 14b has a corresponding recess. The recess of the shell faces the clip 22, which has a corresponding projection. When assembled as shown in FIG. 5B, these alignment features resist separation of the magnets. For example the cushion force acts in a direction shown by arrow 50 whereas the headgear straps apply a force component in the direction shown by arrow 52. The alignment features reduce the effect of this force on separating the magnetic coupling.

In the example shown, the interconnection between the shell 15 and the clip 22 also includes an interlocking feature. The clip 22 has a projection 16 and the shell 15 has a recess 17, thereby defining a male-female interlock. The magnet holds the clip 22 to the shell 15 and the mechanical interlock allows the clip to stay in place when the headgear is tightened and a shear force occurs. Of course, the mechanical interlock can be swapped around.

Of course, any arrangement of projections and recesses can be used.

This embodiment improves the assembly and disassembly of both the clips and cushion. Small rare earth magnets (e.g. a disc of diameter 1 cm and thickness 3 mm) generate pull forces of up to 45N and are relatively inexpensive.

The magnets have been described above only for providing physical coupling of the mask shell and mask cushion, or for physically coupling the strap arrangement. The magnetic coupling elements can also be used as a means to convey electricity or electric signals from one component to another, for example for reading out sensor signals.

The magnetic coupling does not have to define only a single possible connection position, and movable positions are also possible. For the example with magnetic coupling of the strap arrangement for example, the strap positions can be fixed, but the length of the straps can be adjusted. The straps can be fixed for example between two magnetic elements at any position, or a number of magnetic elements in the strap can provide for a number of pre-determined positions.

The magnets are preferably reusable and not disposable. For example, when the seal cushion is disposed of, the magnets should be re-used. This is clearly possible for the magnet arrangements of FIGS. 3A and 3D.

In the claims, any reference signs placed between parentheses shall not be construed as limiting the claim. The word "comprising" or "including" does not exclude the presence of elements or steps other than those listed in a claim. The word "a" or "an" preceding an element does not exclude the presence of a plurality of such elements. The mere fact that certain elements are recited in mutually different dependent claims does not indicate that these elements cannot be used in combination. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

What is claimed is:

1. A patient interface assembly for use in providing a flow of breathing gas to a patient, the patient interface assembly comprising:
    a face contact element including:
        a cushion having a contact surface structured to seal against the face of a patient around one or more of the nose and/or mouth of the patient;
        a frame part coupled to the cushion; and
        a first magnet arrangement disposed on the frame part; and
    a support element including:
        a shell having a front face and a rear face, the front face structured to have a number of headgear straps coupled thereto for securing the support element to the head of the patient, the shell having an aperture defined therethrough from the front face to the rear face that is structured to have a supply conduit coupled thereto for providing the flow of breathing gas; and
        a second magnet arrangement disposed on the shell,
    wherein the frame part of the face contact element is selectively coupleable to the rear face of the shell of the support element via magnetic interaction between the first magnet arrangement and the second magnet arrangement.

2. The assembly as claimed in claim 1, wherein the first magnet arrangement comprises a first magnet disposed on a first side of the frame part and a second magnet disposed on a second side of the frame part, wherein the second magnet arrangement comprises a third magnet disposed on a first side of the shell and a fourth magnet disposed on a second side of the shell, and wherein coupling of the frame part to the shell includes magnetic interaction between (a) the first magnet and the third magnet, and (b) the second magnet and the fourth magnet.

3. The assembly as claimed in claim 2, wherein the first, second, third, and fourth magnets are generally circular shaped.

4. The assembly as claimed in claim 1, wherein the frame part includes a receptacle for containing the first magnet arrangement.

5. The assembly as claimed in claim 1, further comprising an indexing feature associated with the frame part or the shell to facilitate alignment of the frame part to the shell.

6. The assembly as claimed in claim 1, wherein the shell is structured to have the number of headgear straps directly coupled thereto.

7. The assembly as claimed in claim 1, wherein the shell is structured to have each headgear strap of the number of headgear straps indirectly coupled thereto via a clip.

8. The assembly as claimed in claim 1, wherein the number of headgear straps comprises a plurality of headgear straps, wherein the shell is structured to have one headgear strap of the plurality of headgear straps directly coupled thereto, and wherein the shell is structured to have another headgear strap of the plurality of headgear straps indirectly coupled thereto via a clip.

9. The assembly as claimed in claim 1, further comprising a plurality of clips, each clip of the plurality of clips being selectively coupled to the shell and structured to have a headgear strap of the number of headgear straps coupled thereto.

10. The assembly as claimed in claim 1, wherein the shell comprises a plurality of slots defined therein, and wherein each slot of the plurality of slots is structured to have a portion of a strap of the number of straps positioned therein.

11. The assembly as claimed in claim 1, wherein the shell comprises a single piece of material.

* * * * *